United States Patent [19]
Boudewijn et al.

[11] Patent Number: 5,713,851
[45] Date of Patent: Feb. 3, 1998

[54] METHOD FOR MANUFACTURING A CATHETER WITH AT LEAST ONE HIGH-PRESSURE LUMEN

[75] Inventors: Alexander Christiaan Boudewijn, Leek; Tiemen Noppert, Ravenswoud, both of Netherlands

[73] Assignee: Cordis Corporation, Miami Lakes, Fla.

[21] Appl. No.: 574,584

[22] Filed: Dec. 14, 1995

Related U.S. Application Data

[63] Continuation of Ser. No. 269,001, Jun. 30, 1994, abandoned.

[30] Foreign Application Priority Data

Jul. 5, 1993 [NL] Netherlands ............... 9301181

[51] Int. Cl.$^6$ ................................. A61B 17/22
[52] U.S. Cl. ............... 604/35; 604/43; 604/264; 606/159
[58] Field of Search ............... 604/264, 35, 43, 604/38, 44, 45, 266, 267, 269, 280, 53, 282; 606/159, 170; 128/658

[56] References Cited

U.S. PATENT DOCUMENTS

| | | |
|---|---|---|
| 4,100,246 | 7/1978 | Frisch . |
| 4,646,742 | 3/1987 | Packard et al. . |
| 4,715,848 | 12/1987 | Beroza ............... 604/43 |
| 4,981,478 | 1/1991 | Evard et al. ............... 604/282 |
| 5,063,018 | 11/1991 | Fontirroche et al. . |
| 5,116,310 | 5/1992 | Seder et al. . |
| 5,250,069 | 10/1993 | Nobuyoshi et al. ............... 604/282 X |
| 5,254,107 | 10/1993 | Soltesz . |
| 5,290,230 | 3/1994 | Ainsworth et al. . |
| 5,318,518 | 6/1994 | Plechinger et al. ............... 604/43 |
| 5,320,599 | 6/1994 | Griep et al. ............... 604/35 |
| 5,395,315 | 3/1995 | Griep ............... 604/35 |
| 5,437,632 | 8/1995 | Engelson ............... 604/280 X |
| 5,445,624 | 8/1995 | Jimenez ............... 604/280 |
| 5,460,608 | 10/1995 | Lodin et al. ............... 604/282 X |

FOREIGN PATENT DOCUMENTS

| | | |
|---|---|---|
| 2530958 | 7/1992 | France . |
| 32 39 032 A1 | 10/1982 | Germany . |

OTHER PUBLICATIONS

Netherlands Application Examination Report—9301181—5 Jul. 1993.

*Primary Examiner*—Michael Powell Buiz
*Assistant Examiner*—N. Kent Gring
*Attorney, Agent, or Firm*—Gerstman, Ellis & McMillin, Ltd.

[57] ABSTRACT

A method of manufacturing a catheter which comprises a pair of separate lumens defining a higher pressure lumen and a lower pressure lumen, plus a side opening positioned adjacent the distal end of the catheter and communicating with the lower pressure lumen. A relatively thin tube defines the higher pressure lumen. One incorporates the relatively thin tube into a lumen of a relatively thick tube, followed by forming of the distal end of the high pressure lumen to curve rearwardly to form a proximally extending section having a proximal end. One then forms the side opening at a position adjacent the proximal end of the proximally extending section. The relatively thin tube may carry fibrous reinforcement to facilitate its use in defining the higher pressure lumen.

16 Claims, 3 Drawing Sheets

METHOD FOR MANUFACTURING A CATHETER WITH AT LEAST ONE HIGH-PRESSURE LUMEN

This is a continuation of U.S. application Ser. No. 08/269,001, filed Jun. 30, 1994 now abandoned.

BACKGROUND OF THE INVENTION

The invention relates to a method for making a catheter with at least one high-pressure lumen. Such a catheter is for example known from EP-A-0 442 579 and Griep et al. U.S. Pat. No. 5,320,599. The hydrothrombectomy catheter described therein comprises a high-pressure lumen which bends back at the distal end and ends in a nozzle which is directed along an opening in the low-pressure lumen. By supplying a liquid under high pressure through the high-pressure lumen close to the opening in the low-pressure lumen, a suction is created by ejector or aspiration action with which for example thrombi can be removed.

The object of the invention is to provide a method for manufacturing such a catheter.

DESCRIPTION OF THE INVENTION

The process of the invention is characterized by using a separate, thin tube with a high-pressure resistant sheath which defines a high-pressure lumen. The catheter can withstand very high pressures in the high-pressure lumen. A thicker tube in which the thin tube is incorporated can be manufactured of a different material, for instance a less pressure-resistant and more pliable material, so that the manufactured catheter will nevertheless display the required flexibility.

The thin tube may be used as mandrel around which the thicker tube is extruded.

Alternatively, the thin tube can be inserted into the thicker one during a final stage of manufacturing the catheter, whereby the tubes typically each have a length matching the length of the catheter to be manufactured.

The thicker tube typically defines two or more lumens. One of the lumens is occupied by the thin tube to form a high-pressure lumen which is reinforced by the strong wall of the thin tube, which may be further reinforced with a braided strand tubular reinforcement or the like. The other lumen of the thicker tube may serve as a low pressure lumen and preferably has a maximum effective cross-section. The thin tube can very easily be incorporated in the thicker one, typically being partially surrounded by the low-pressure lumen.

In order to obtain a required compression resistance of the thin tube, reinforcement of the plastic material of the thin tube can be achieved by employing a known extrusion-method wherein, during the extrusion, threads of a plastic material, which in solidified state have a high tensile strength, may be extruded typically in crossing, helically shaped strands in the extrusion process. Alternatively, conventional plastic or metal braided tubing may be added, which, due to the reinforcing strands, may have a very high compression resistance.

DESCRIPTION OF THE DRAWINGS

The invention will be explained in greater detail in the following description with reference to the attached drawings.

DESCRIPTION OF SPECIFIC EMBODIMENTS

Figure 1:
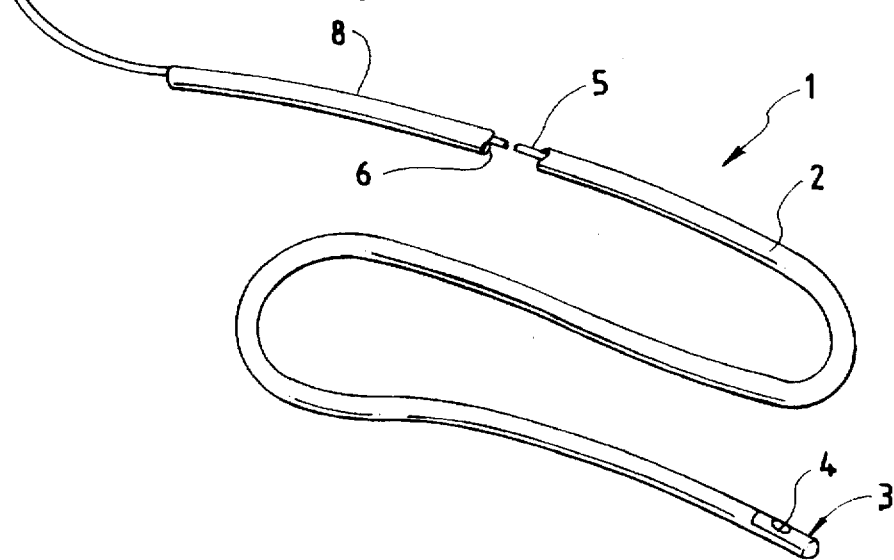
FIG. 1 shows schematically part of a catheter manufactured by the method of the invention.

The catheter 1, partly shown in FIG. 1, comprises in the usual manner a basic body 2 with a distal end 3 which is introduced into the body of a patient during treatment. The conventional, proximal end, to which the connecting pieces have been attached, is not shown in FIG. 1.

The catheter 1 is of the thrombectomy type, and has an opening 4 in the distal end 3 through which for example blood clots can be removed from the body of a patient. With this catheter the suction is generated by an ejector or aspiration action at the opening 4, which is achieved as a liquid jet 36 (FIG. 8) inside the catheter is directed along the opening 4, for example in accordance with Griep et al. U.S. Pat. No. 5,320,599, the disclosures of which are incorporated herein by reference.

The liquid for liquid jet 36 is supplied through tube 5 defining high-pressure lumen 9, which bends back at the distal end 3 of the catheter 1 and ends in nozzle or jet 36 which is directed axially along catheter 1, across opening 4.

With the catheter 1, which has been manufactured by a method of the invention, the high-pressure lumen 9 is formed in a separate, thin tube-like element 5 which has been placed in a thicker tube element 8. Also, a low-pressure lumen 6 is formed in thicker tube 8, which is connected to opening 4. The lower-pressure lumen 6 and the high-pressure lumen 9 are connected to connecting pieces such as a Y-connector at the proximal end of catheter 1 in a usual manner.

The thin tube 5 has a high-pressure braided wire tubular reinforcement 12 surrounding or within it, so that a high pressure can be generated in high pressure lumen 9, so that although the cross-section of this lumen is small, a considerable liquid flow can be generated.

Figure 2:
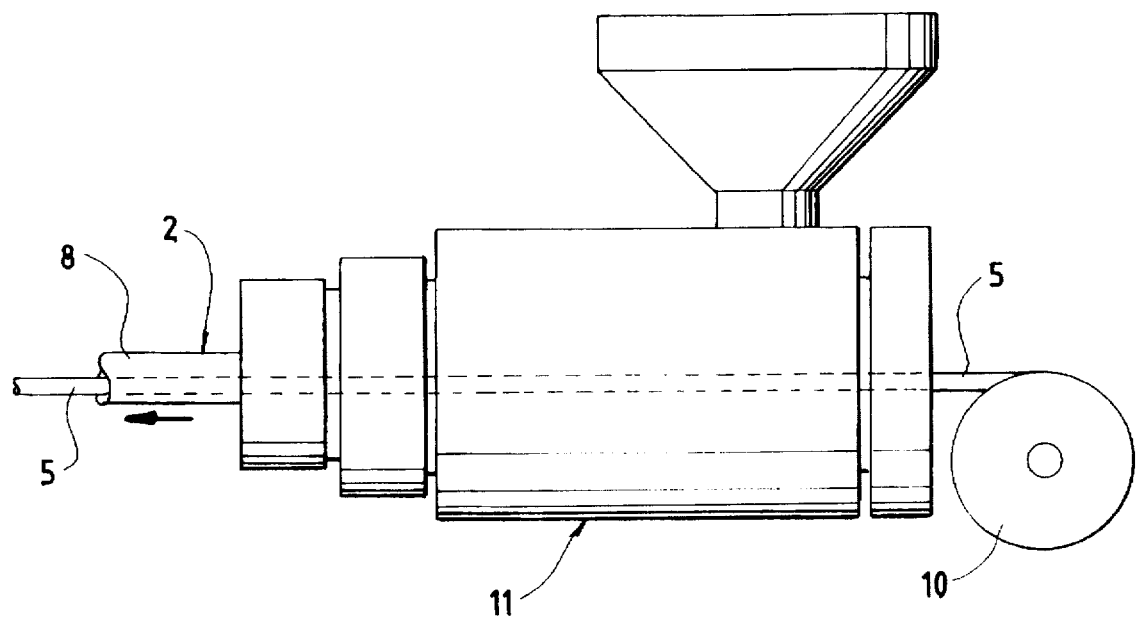
FIG. 2 illustrates schematically a manufacturing method of the invention.

FIG. 2 shows schematically a manufacturing method according to an embodiment of the invention.

A substantial length of thin tube 5 has been manufactured beforehand by means of an extrusion process for instance. The material and fibrous reinforcement used is such that the required high-pressure resistance of the thin tube 5 is obtained.

The manufactured thin tube 5 is wound on a storage reel 10 and is fed through a schematically illustrated extrusion machine 11. The thin tube 5 can function as a mandrel during the extrusion of the thick tube body 8 around it. The thin tube 5 is incorporated into the thick tube 8 as the thick tube is extruded around the thin tube.

Thus a great length of catheter material can be manufactured comprising a thick tube 8 having thin tube 5 incorporated in it.

Figure 3:
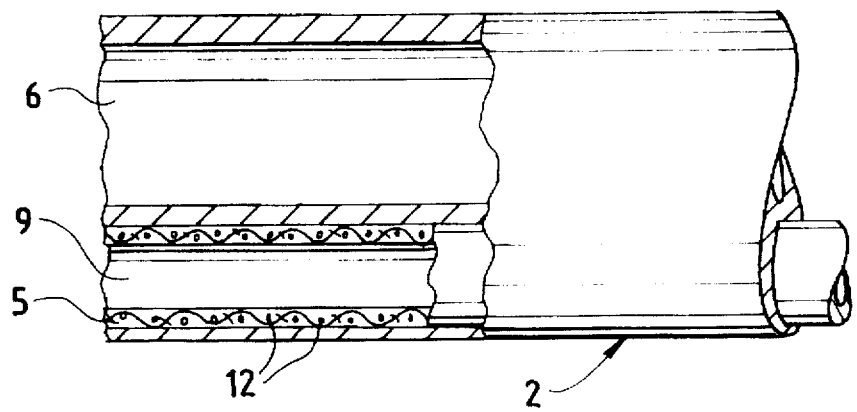
FIG. 3 shows, partly in a longitudinal cross-section, part of the catheter of FIG. 1 manufactured by the method of the invention.

FIG. 3 shows the product made in this way in greater detail.

The sheath of the thin tube 5 may comprise a reinforced plastic material. More in particular, this element 5 has been made up of an inner basic layer of a suitable plastic material, a reinforcing layer of thin metal wire 12 braided or wound around it, and surrounding it all an outer layer of plastic material. Such a method for manufacturing a pressure resistant tube is in itself known for making catheters.

The thicker tube 8, with the thin tube 5 incorporated therein, is formed with two channels or lumens. The first lumen 7 is formed around the thin, pressure resistant tube 5. The other lumen 6 forms the larger, low-pressure lumen.

Figure 5:
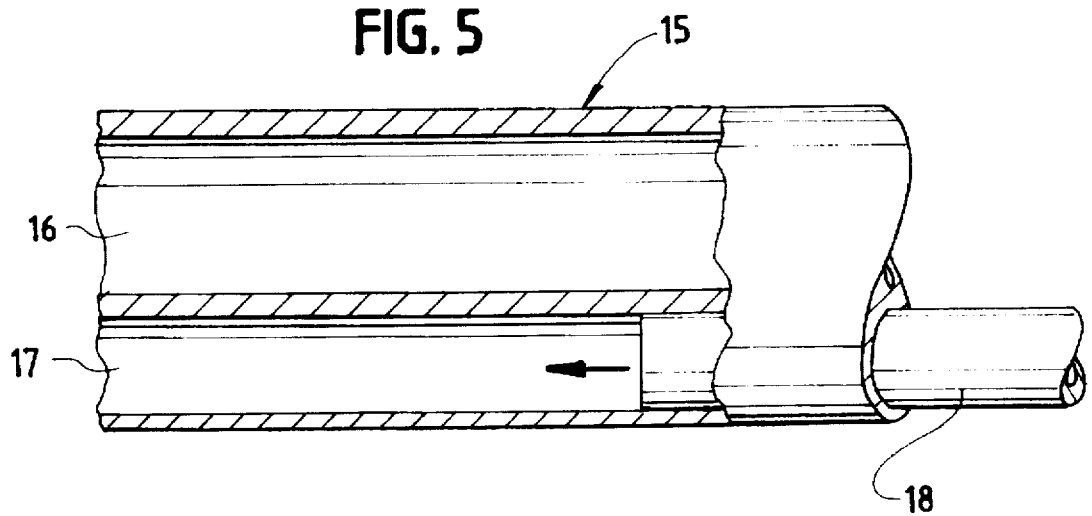
FIGS. 5 and 6 represent views of a catheter manufactured by another method of the invention corresponding to FIGS. 3 and 4.

FIG. 5 illustrates another manufacturing method for the catheter shown herein. The thicker tube 15 is extruded separately with two channels 16 and 17. The channel 16 defines the low-pressure lumen, and the channel 17 slidingly receives the thin tube 18 with the high-pressure lumen. During the manufacturing process, suitable lengths of the thin tube 18 and the thicker tube 15 are taken from a supply, and the thin tube 18 is pulled or pushed into the channel 17, which is made for this purpose. In order to be able to pull the tube 18 properly into the channel 17, the thinner tube 18 can be stretched, for instance by pulling it from two sides over a mandrel inserted in channel 9. Consequently the diameter of the tube 18 will decrease slightly. After inserting the thin tube 18, the thin tube 15 is released again, as result of which the thin tube 18 will be stuck tightly inside the channel 17. A lubricant can of course be used in order to facilitate this insertion process.

Figure 6:
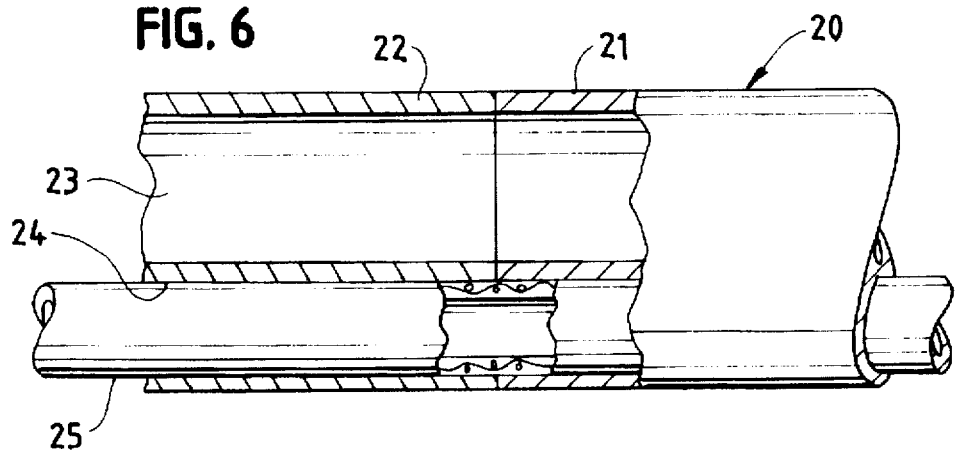

The catheter 20, shown in FIG. 6, has been manufactured in this manner. Also, in this embodiment, the thicker tube may be made up of a plurality of aligned, abutting tube sections 21 and 22. The sections 21 and 22 may have different material properties and formulations so that, for instance, the constituent sections become more pliable towards the distal end.

Figure 4:
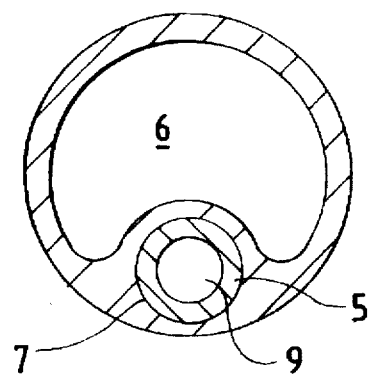
FIG. 4 shows a cross-section of FIG. 3.

Each of the tube sections 21 and 22 has a cross-section corresponding to the cross-section of the overall catheter, shown as the thicker composite tube part 8, in FIG. 4. The lumen 23 with the largest bore forms in this case once again the low-pressure lumen, and the lumen 24 houses the thin, high-pressure tube 25. The different, preformed parts 21, 22 are placed against each other end to end, and connected to each other and tube 25, for instance by gluing or heat welding.

Although catheter embodiments have been described here comprising one high-pressure lumen and one low-pressure lumen, other configurations are possible as well. A catheter may comprise several high-pressure lumens and also several low-pressure lumens. The illustrated embodiments are specifically, however, improvements for the described catheter of Griep et al. U.S. Pat. No. 5,320,599.

Figure 7:
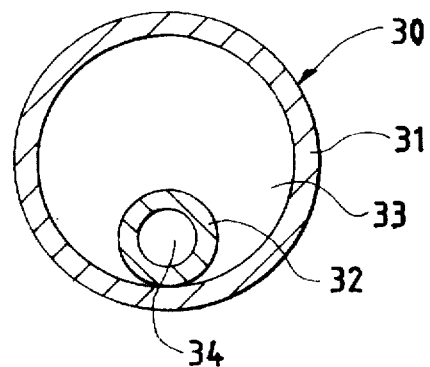
FIG. 7 shows a cross-section of a catheter manufactured by yet another method of the invention, to make a catheter corresponding to FIGS. 3 and 4.

With the embodiment of FIG. 7, the thin, tube 32, having a high-pressure resistant, fibrous sheath as previously described, has been incorporated into a thicker tube 31 which defines only one large lumen 33 that is at least twice the diameter of thin tube 32. That part of lumen 33 not occupied by the thin tube 32 forms in that case the low-pressure lumen.

This catheter 30, can be easily manufactured simply by pushing the thin tube 32 into the lumen 33 of the thicker tube 31. The cross-section of the remaining low-pressure lumen 33 has in this embodiment a maximum possible dimension, as no additional material is present for housing or retaining the thin tube 32, which defines the high-pressure lumen 34.

The thicker tube 31 of this embodiment can be manufactured cheaply, so that the entire catheter manufactured in this way is very economical for use.

As mentioned before, the thicker tube can be manufactured of a relatively flexible, soft material, as this material itself is not subjected to high pressures. Thus the catheter manufactured according to this invention can display the required flexibility.

Figure 8:
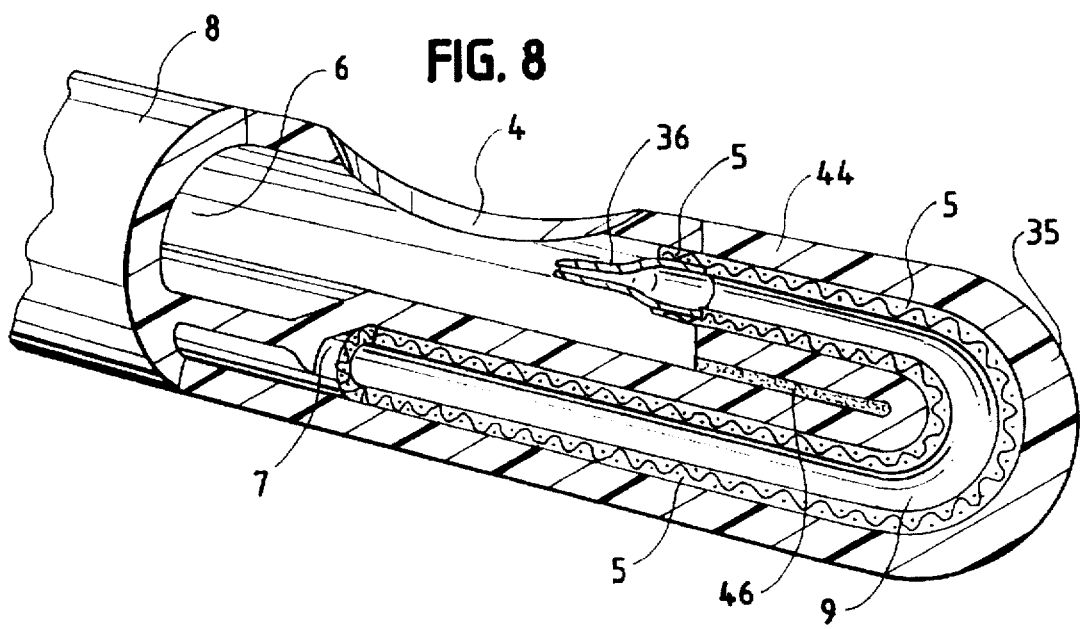
FIG. 8 is a fragmentary, perspective view of the distal end of the catheter of FIG. 1.

Referring to FIG. 8, details of the catheter distal tip in accordance with this invention are shown. The design of FIG. 8 may be utilized with each of the embodiments disclosed in previous drawings, but is specifically shown as a further detail of the embodiment of FIGS. 1, 3 and 4.

The tubing 5 which forms high pressure lumen 9 has a distal portion 44 which is folded about itself by 180°, with a jet or nozzle 36 being positioned in the lumen of tube 7. Alternatively, nozzle 36 may be J or U-shaped in a configuration similar to that disclosed in U.S. Pat. No. 5,320,599. At the distal portion 44, portions of the wall of thicker tube 8 which defines low pressure lumen 6 may be cut away as needed. Aperture 4 is cut in the thicker tube wall 8 adjacent the tip of jet nozzle 36 for outside access of what becomes the distal end of low pressure lumen 6 in the area of the nozzle outlet. The distal end of tube 8 is closed around nozzle 36 using a heated die, and the folded configuration may be secured together by adhesive 46.

Thus, pressurized fluid may be passed through high pressure lumen 9, to extend around 180 degree bend 35 in or into nozzle 36 at a high velocity. As taught in U.S. Pat. No. 5,320,599, the fluid jet from nozzle 36 is directed proximally through low pressure lumen 6 across side aperture 4, exerting in this mode of operation a suction through aperture 4 by ejector or aspiration action. Thus, materials outside of the catheter and adjacent aperture 4 may be sucked in through aperture 4 and conveyed proximally through low pressure lumen 6, along the catheter and out of the body.

However, if a proximal portion of the low pressure lumen 6 is intentionally obstructed, then fluid from nozzle 36 will flow with turbulence out of aperture 4 to bathe the tissues and to pick up materials desired for removal from the immediate area of the body. Following this, the obstruction of lumen 6 may be removed, causing the ejector or aspiration action to resume through nozzle 36 into low pressure lumen 6, creating again a resulting gentle suction for removal of fluids and the materials picked up by the fluids from the body, with the fluids passing once again through aperture 4 and proximally along lumen 6.

The above has been offered for illustrative purposes only, and is not intended to limit the scope of the invention of this application, which is defined in the claims below.

That which is claimed:

1. The method of manufacturing a catheter which comprises a pair of separate lumens defining a higher pressure lumen and a lower pressure lumen, and further defining a side opening adjacent the distal end of said catheter, which side opening communicates with the lower pressure lumen, said higher pressure lumen extending distally of said side opening and curving rearwardly again to define a jet nozzle positioned adjacent said side opening to direct fluids from the higher pressure lumen across said side opening into the lower pressure lumen, comprising the steps of:

provinding a relatively think flexible tube which carries a tube of reinforcing fibers for strength increase to define the higher pressure lumen; extruding a multiple-lumen, relatively thick tube having a distal end about said thin, flexible tube; causing the distal end of the high pressure lumen to curve rearwardly to form a proximally extending section having a proximal end; and forming said side opening at a position adjacent the proximal end of said proximally extending section through said relatively thick tube so that the side opening communicates with an open lumen of the relatively thick tube.

2. The method of claim 1 in which said relatively thin tube defines a distal end which comprises a jet nozzle.

3. The method of claim 1 in which said reinforcing fibers are made of plastic and are helically wound with said thin tube during manufacture of said thin tube.

4. The method of claim 1 in which said relatively thin tube carries a tubular layer of braided metal fibers for strength increase.

5. The method of claim 1 in which said relatively thin tube is of substantially the length of said relatively thick tube.

6. The method of manufacturing a catheter which comprises a pair of separate lumens defining a higher pressure lumen and a lower pressure lumen, and further defining a side opening adjacent the distal end of said catheter, which side opening communicates with the lower pressure lumen, said higher pressure lumen extending distally of said side opening and curving rearwardly again to define a jet nozzle positioned adjacent said side opening to direct fluids from the higher pressure lumen across said side opening into the lower pressure lumen, comprising the steps of:

providing a relatively think flexible tube which carries a tube of reinforcing fibers for strength increase to define the higher pressure lumen; incorporating said relatively thin tube into at least most of the length of one lumen of a relatively thick tube having a distal end; said one lumen having at least twice the diameter of said relatively thin tube; causing the distal end of the thin, flexible tube to curve rearwardly to form a proximally extending section having a proximal end; and forming said side opening at a position adjacent the proximal end of said proximally extending section so that the side opening communicates with the one lumen of the relatively thick tube.

7. The method of claim 6 in which said relatively thin tube defines a distal end which comprises a jet nozzle.

8. The method of claim 6 in which said reinforcing fibers are made of plastic and are helically wound with said thin tube during manufacture of said thin tube.

9. The method of claim 6 in which said relatively thin tube carries a tubular layer of braided metal fibers for strength increase.

10. The method of claim 6 in which said relatively thin tube is of substantially the length of said relatively thick tube.

11. The method of manufacturing a catheter which comprises a pair of separate lumens defining a higher pressure lumen and a lower pressure lumen, and further defining a side opening positioned adjacent the distal end of said catheter, which side opening communicates with the lower pressure lumen, said higher pressure lumen extending distally of said side opening and curving rearwardly again to define a jet nozzle positioned adjacent said side opening to direct fluids from the higher pressure lumen across said side opening into the lower pressure lumen, comprising the steps of: providing a relatively thin, flexible tube to define the higher pressure lumen; incorporating said relatively thin tube into a closely-fitting lumen of a relatively thick, multiple lumen tube having a distal end; causing the distal end of the relatively thin tube to curve rearwardly to form a proximally extending section having a proximal end; and forming said side opening at a position adjacent the proximal end of said proximally extending section, said relatively thick tube comprising of series of separate, abutting tubular sections, said tubular sections being secured to each other and to the relatively thin tube carried within said relatively thick tube, said separate, abutting tubular sections being made of flexible materials having differing physical properties.

12. The method of claim 11 in which said relatively thin tube defines a distal end which comprises a nozzle.

13. The method of claim 11 in which said relatively thick tube is formed about said relatively thin tube by extrusion.

14. The method of claim 11 in which said relatively thin tube has reinforcing fibers which are helically wound with said thin tube during manufacture of said thin tube.

15. The method of claim 11 in which said relatively thin tube carries a tubular layer of braided metal fibers for strength increase.

16. The method of claim 11 in which said relatively thin tube is of substantially the length of said relatively thick tube.

* * * * *